Sept. 19, 1939. W. I. JOHNSTON Plant Pat. 339
ROSE PLANT
Filed Dec. 17, 1938
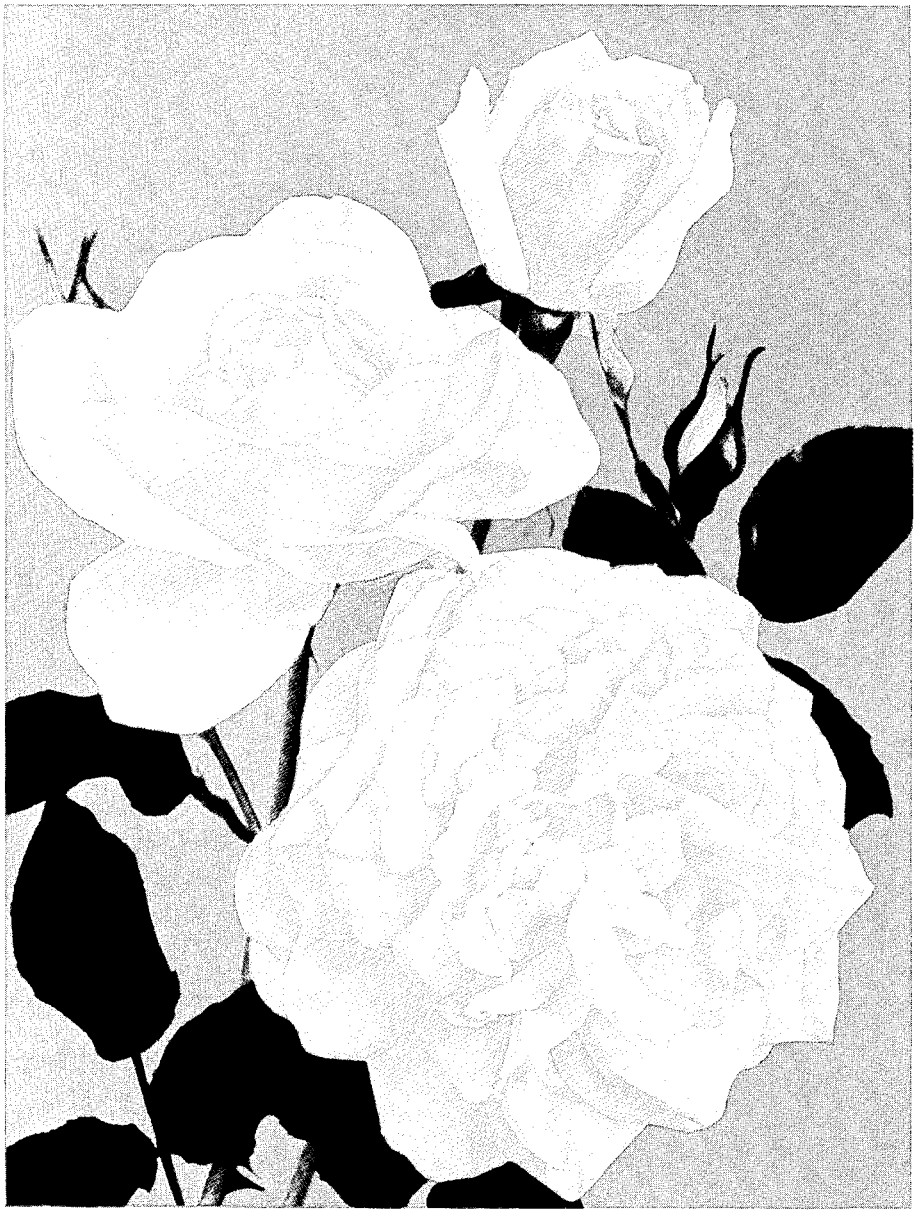
Inventor
Walter Irwin Johnston
By Robbins & Robbins
Attorneys Patented Sept. 19, 1939

Plant Pat. 339

UNITED STATES PATENT OFFICE

339

ROSE PLANT

Walter Irwin Johnston, Portadown, Ireland, assignor to Jackson & Perkins Company, Newark, N. Y.

Application December 17, 1938, Serial No. 246,469

1 Claim. (Cl. 47—61)

This invention relates to a new and distinct variety of rose plant of the Hybrid Tea class.

The original drawing depicts the flower of this new variety substantially in natural size and at different stages of development from bud to full bloom rose. From this it will be observed that the features which make it an outstanding novelty are the large capucine orange flower, unusually large in that range of color, and the pleasing effect of this coloring in the combination shades of the various stages of development.

In addition to the foregoing, the new variety is distinguished by the long lasting quality of the flowers, the very vigorous growing of the bush as well as the very vigorous and healthy character of the foliage.

The plant has been asexually reproduced and its characteristics referred to have been found to be fixed.

The following is a detailed description of the new variety, all color terminology being in accordance with Ridgway's Color Standard:—

Parentage:
*Seed parent.*—Angele Pernet.
*Pollen parent.*—Mrs. Charles Lamplough.
Classification:
*Botanic and commercial.*—Hybrid Tea.

*Flower*

(Observations made at Newark, New York, in the morning of June 23rd, 1938.)

Blooming habit:
Recurrent—continuous.
Bud:
*Size.*—Large.
*Form.*—Short; globular; is not affected by wet or hot weather.
*Color.*—When sepals first divide—Plate 1, Rose Doree. When petals begin to unfurl—Plate 2, Grenadine. When half blown: inside of petals—Plate 2, Bittersweet Orange; reverse of petals—Plate 2, Bittersweet Pink.
*Sepals.*—Branched; curl back when color appears. Color—Rainette Green, Plate 31.
*Calyx.*—Shape—funnel with tips extending beyond the point of the bud until the color of the flower begins to show and then they fold away; size—broad; aspect—smooth; odor when rubbed—none.
*Peduncle.*—Length—medium; aspect—smooth; color—Plate 31, Rainette Green. Strength—stiff.
*Opening.*—Bud opens well; is not affected by adverse conditions.

Bloom:
*Size.*—Large.
*Average size when fully expanded.*—Four and one-half inches.
*Borne.*—Singly.
*Stems.*—Long, strong.
*Form.*—When first open—cupped. Permanence—retains its form to the end, flattens somewhat.
*Petalage.*—Double (full but open center). Number of petals under normal conditions—40 to 50.
*Color.*—Center of flower—Plate 3, Capucine Orange. Outer petals—Plate 3, Orange Buff. Base of petals (aiglet)—Plate 4, Light Cadmium. Inside of petals—Plate 2, Grenadine. Reverse of petals—Plate 2, Bittersweet Pink.
*Variegations.*—None.
*Discoloration.*—General tonality at end of first day: fades—gradually lighter.

Petals:
*Texture.*—Thin; is not affected by wet or hot weather.
*Appearance.*—Inside—satiny; outside—shiny.
*Form.*—Oval, scalloped.
*Arrangement.*—Imbricated (regularly arranged shinglelike). Petaloids in center—many, small.
*Persistence.*—Drop off cleanly.
*Fragrance.*—Strong. Nature—Tea (average Hybrid Tea scent).
*Lasting quality.*—On the plant and as cut flowers, long.

Genital organs:
*Stamens, anthers.*—Medium size, many; color—Plate 4, Light Cadmium; arrangement—regular around styles.
*Stamens, filaments (threads).*—Long; color—Plate 4, Lemon Chrome.
*Pollen.*—Plate 4, Buff Yellow.
*Styles.*—Loosely separated, uneven length; medium length, thin.
*Stigmas.*—Plate 4, Empire Yellow.
*Ovaries.*—All enclosed in calyx.

Fruit:
Variety is fertile.
*Form.*—Funnel shaped.
*Aspect.*—Smooth.
*Sepals.*—Permanent; recurved.

Form:
Bush.

Growth:
Very vigorous.

Foliage:
5 to 7 leaflets.
*Size.*—Large.
*Quantity.*—Normal.
*Color.*—New foliage: upper side—Plate 1, Maroon; under side—Plate 13, Vandyke Red. Old foliage: upper side—Plate 31, Dark Cress Green; under side—Plate 31, Light Cress Green.
*Shape.*—Oval.
*Texture.*—Upper side—glossy; under side—rough. Ribs and veins—ordinary.
*Edge.*—Serrated (saw toothed).
*Serration.*—Single, small, sharp.
*Rachis.*—Color—Plate 31, Rainette Green. Under side—prickles.
*Stipules.*—Medium length; smooth.
*Disease resistance.*—Resistant.
Wood:
*New wood.*—Color—Jade Green, Plate 31. Bark—smooth.
*Old wood.*—Color—Plate 31, Rainette Green. Bark—smooth.
Thorns (divided into thorns, prickles and short needles):
*Thorns.*—Quantity: on main stalks from base—ordinary; on laterals from stalk—few. Form—broad base, hooked downward; long. Color when young—Plate 27, Corinthian Red. Position—in sets of three.
*Prickles.*—Quantity: on main stalks—few; on laterals—few. Color—Plate 27, Corinthian Red.
*Short needles.*—Quantity: on main stalks and laterals—none.

I claim:

A new and distinct variety of rose plant, characterized as to novelty by the very vigorous growing habit of bush and foliage, and by its large size capucine orange flowers, substantially as shown and described.

WALTER IRWIN JOHNSTON.